(12) United States Patent
Murakami et al.

(10) Patent No.: US 7,645,796 B2
(45) Date of Patent: Jan. 12, 2010

(54) AMINO ACID COMPOSITION PROMOTING COLLAGEN SYNTHESIS

(75) Inventors: Hitoshi Murakami, Kawasaki (JP); Hisamine Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 619 days.

(21) Appl. No.: 11/477,436

(22) Filed: Jun. 30, 2006

(65) Prior Publication Data

US 2006/0247313 A1 Nov. 2, 2006

Related U.S. Application Data

(62) Division of application No. 11/092,890, filed on Mar. 30, 2005, now abandoned.

(30) Foreign Application Priority Data

Apr. 1, 2004 (JP) ............................ 2004-109506

(51) Int. Cl.
*A61K 31/195* (2006.01)
(52) U.S. Cl. ...................... 514/561; 514/563
(58) Field of Classification Search ................. 514/561, 514/563
See application file for complete search history.

(56) References Cited

U.S. PATENT DOCUMENTS

| 5,326,569 | A | 7/1994 | Acosta et al. |
| 5,576,351 | A | 11/1996 | Yoshimura et al. |
| 5,719,119 | A | 2/1998 | Veech |
| 5,733,884 | A | 3/1998 | Barbul et al. |
| 6,048,846 | A | 4/2000 | Cochran |
| 6,221,836 | B1 | 4/2001 | Beale et al. |
| 6,346,264 | B1 | 2/2002 | White |
| 6,511,696 | B2 | 1/2003 | Gohman et al. |
| 6,864,242 | B2 | 3/2005 | Ernest |
| 2003/0091601 | A1 | 5/2003 | Barbul |
| 2004/0058309 | A1 | 3/2004 | Washizu et al. |

FOREIGN PATENT DOCUMENTS

| BE | 669090 | 3/1966 |
| EP | 0 197 514 | 10/1986 |
| EP | 0 560 989 | 9/1993 |
| GB | 1050756 | 12/1966 |
| WO | 00/62789 | 10/2000 |
| WO | 02/087562 | 11/2002 |
| WO | 03/016520 | 2/2003 |

OTHER PUBLICATIONS

Georges Bellon et al, "Glutamine increases collagen gene transcription in cultured human fibroblasts", *Biochimica et Biophysica Acta*, 1268, pp. 311-323 (1995).

Jeremy Z. Williams et al, "Effect of a Specialized Amino Acid Mixture on Human Collagen Deposition", *Annals of Surgery*, vol. 236, No. 3, pp. 369-375 (2002).

*Primary Examiner*—Raymond J Henley, III
(74) *Attorney, Agent, or Firm*—Oblon, Spivak, McClelland, Maier & Neustadt, L.L.P.

(57) ABSTRACT

Herein are disclosed an excellent collagen synthesis-promoting amino acid composition that are characterized by containing specific amino acids at a specific ratio, more specifically, by containing 10-40 parts by weight of L-arginine and/or 10-40 parts by weight of L-glutamine, as well as 5-20 parts by weight of L-valine, 8-30 parts by weight of L-isoleucine and 10-35 parts by weight of L-leucine, an amino acid composition that inhibits skin aging, an amino acid composition that suppresses osteoporosis, an amino acid composition that promotes regeneration of tendon and ligament, and an amino acid composition that heals wounds or thermal burns, that are of the same composition.

16 Claims, 1 Drawing Sheet

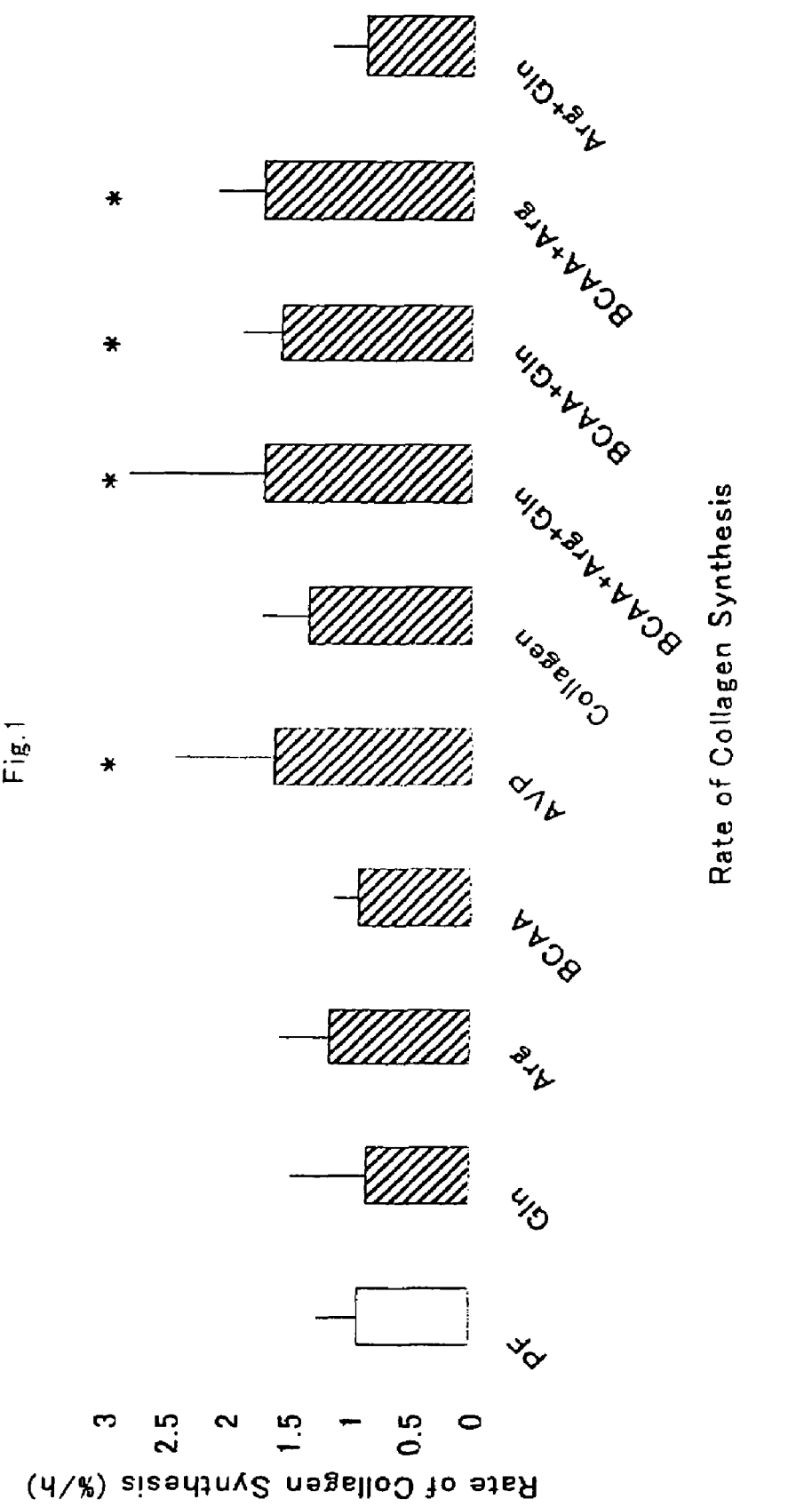

AMINO ACID COMPOSITION PROMOTING COLLAGEN SYNTHESIS

FIELD OF THE INVENTION

The present invention relates to an amino acid composition that promotes collagen synthesis, and which composition comprises 5 or 4 kinds of specific amino acids, namely, L-arginine and/or L-glutamine, as well as L-valine, L-isoleucine and L-leucine, at a specific ratio, and also to an amino acid composition that are useful for inhibiting skin aging, suppressing osteoporosis, promoting regeneration of tendon and ligament, and healing wounds or thermal burns, that are associated with collagen synthesis.

BACKGROUND ART

Collagen, the protein that is present in the largest amount in a human body, plays an extremely important role as connective tissue that is a component of the extracellular matrix. Examples of tissue that contain large quantities of collagen include skin, bone tissue, tendon, ligament, and the like. As these tissues age, wrinkles or sagging, osteoporosis and the like are caused, and the major cause of these is thought to be a decrease in amount, degeneration or the like of tissue collagen.

It is known that collagen synthesis is stimulated by the action of vitamins, hormones, cytokines and the like, and it is also known that amino acids that are the building blocks of proteins also promote collagen synthesis. It has been reported from studies using fibroblasts that glutamine promoted collagen synthesis (G. Bellon et al., Biochimica Biophysica Acta, 1995, 1268, 311-323), and also from studies of wound healing using humans or animals that arginine alone or a mixture of arginine, β-hydroxy-β-methylbutyric acid, and glutamine promoted collagen synthesis at wound sites (US005733884A, US20030091601A1, and J. Z. Williams et al., Annals of surgery, 2002, 369-375).

Further, although collagen protein or a collagen-composing amino acid composition and the like are commercially available as products that promote collagen synthesis, the effects of these are not clear, and a demand exists for amino acids or an amino acid composition that possesses an excellent effect.

DISCLOSURE OF THE INVENTION

[Problems to be Solved by the Invention]

In the background of the foregoing background art section, it is an object of the present invention to provide an amino acid composition having an excellent action for promoting collagen synthesis.

[Means for Solving the Problems]

The present inventors have carried out concentrated studies to solve the problem described above, and found as the results thereof that an amino acid composition which contains 5 kinds or 4 kinds of amino acids selected from the group consisting of L-arginine and/or L-glutamine, as well as L-valine, L-isoleucine and L-leucine at a specific ratio, promotes collagen synthesis. On these findings have they completed the present invention.

Accordingly, the present invention relates to a collagen synthesis-promoting amino acid composition that are characterized by containing specific amino acids at a specific ratio, more specifically, by containing 10-40 parts by weight of L-arginine and/or 10-40 parts by weight of L-glutamine, as well as 5-20 parts by weight of L-valine, 8-30 parts by weight of L-isoleucine and 10-35 parts by weight of L-leucine, and also to an amino acid composition that inhibits skin aging, an amino acid composition that suppresses osteoporosis, an amino acid composition that promotes regeneration of tendon and ligament, and an amino acid composition that heals wounds or thermal burns, that are of the same composition.

[Effect of the Invention]

According to the compositions of 5 or 4 specific amino acids of the present invention, collagen synthesis is promoted in a body such as in the skin or the bone tissue.

BRIEF DESCRIPTION OF DRAWINGS

FIG. 1 shows the variations in the rate of collagen synthesis, depending upon the amino acids make-up.

BEST MODE FOR CARRYING OUT THE INVENTION

The amino acid composition of the present invention is characterized in that it contains 10-40 parts by weight of L-arginine and/or 10-40 parts by weight of L-glutamine, as well as 5-20 parts by weight of L-valine, 8-30 parts by weight of L-isoleucine and 10-35 parts by weight of L-leucine. In this connection, the amino acids to be utilized in the present invention can be peptides containing these amino acids.

The inventive amino acid composition may be compounded with suitable additives, for example, other nutrients such as carbohydrates, lipids, proteins, vitamins, minerals, and the like, or a combination of two or more of these. An excipient, a taste-improving agent, a coloring agent or the like may also be combined therewith. An amino acid composition of the present invention that is produced in this manner can be put on the market for distribution in that state, that is, in the form of a powder or liquid mixture. The amino acid composition can also be put on the market for distribution, for example, in the form of a supplement, a condiment, a processed food, a pharmaceutical such as a transfusion or the like.

An amino acid composition of the present invention may, naturally, be administered orally, and may also be administered by intravenous injection. It need hardly be said that for administration by intravenous injection, the amino acid composition is formulated in a form where additives that are unsuitable for intravenous injection have been excluded.

An amino acid composition of the present invention may be administered at a daily dose of approximately 5 to 12 g per adult regardless of whether orally or intravenously, in consideration of cases in which it could be administered orally to a rat to give the same degree of increase in blood level of amino acids as achieved when it was administered intravenously with a promoted collagen synthesis observed.

The amino acid composition of the present invention can be administered by the method and at a dose described above, for example, at a time when there is a risk of the onset of symptoms of skin aging or osteoporosis, or when the symptoms have already appeared, thereby to prevent the onset or suppress progression of the symptoms, and also to improve the symptoms.

EXAMPLE

SD (IGS) male rats consisting of 4 to 6 individuals per group were fed protein-free food (0% casein) for one week to groups of, after which the rats were used in the following experiments. A total of 10 groups were established as test groups for amino acid administration, which groups were respectively administered with: 1) physiological saline, 2) L-glutamine, 3) L-arginine, 4) a composition of 3 kinds of branched chain amino acids (L-leucine, L-isoleucine and L-valine, also collectively referred to as "BCAA"), 5) a composition of 12 kinds of amino acids (L-isoleucine, L-leucine, L-valine, L-glutamine, L-histidine, L-lysine, L-phenylalanine, L-proline, L-threonine, L-methionine, L-tryptophan and L-arginine), 6) a composition of amino acids composing collagen (L-isoleucine, L-leucine, L-valine, L-histidine, L-lysine, L-phenylalanine, L-proline, L-hydroxyproline, L-threonine, L-methionine, L-alanine, L-aspartic acid, L-glutamic acid, L-glycine, L-serine and L-arginine), 7) a composition of 5 kinds of amino acids (L-leucine, L-isoleucine, L-valine, L-glutamine and L-arginine), 8) a composition of 4 kinds of amino acids #1 (L-leucine, L-isoleucine, L-valine and L-glutamine), 9) a composition of 4 kinds of amino acids #2 (L-leucine, L-isoleucine, L-valine and L-arginine), and 10) a composition of 2 kinds of amino acids (L-arginine and L-glutamine) The amino acid compositions and administered concentrations are shown in Table 1 hereunder.

ΔEf: labelled percentage of the free phenylalanine in the skin tissue fluid per unit time ΔT: unit time FIG. 1 shows the variations in the rate of collagen synthesis. The results revealed that for the groups administered with the composition or mixture of 5 kinds of amino acids (denoted by "BCAA+Arg+Gln" in the FIGURE), the composition of 4 kinds of amino acids #1 (denoted by "BCAA+Gln" in the FIGURE) or the composition of 4 kinds of amino acids #2 (denoted by "BCAA+Arg" in the FIGURE), the rate of collagen synthesis was significantly enhanced in comparison with the group administered with physiological saline (denoted by "PF" in the FIGURE) Further, because a enhancement from saline was not observed for the group administered with the composition of branched chain amino acids (denoted by "BCAA" in the FIGURE), L-arginine (denoted by "Arg" in the FIGURE), L-glutamine (denoted by "Gln" in the FIGURE) or the mixture of L-arginine+ L-glutamine (denoted by Arg+Gln in the FIGURE), and the rate of collagen synthesis was promoted for the group administered with the mixture of

TABLE 1

| Amino Acid Make-up of the Administered Fluids, and Administered Concentration | | | | | | | | |
|---|---|---|---|---|---|---|---|---|
| | 5 kinds of amino acid mixture | 4 kinds of amino acid mixture #1 | 4 kinds of amino acid mixture #2 | 12 kinds of amino acid mixture | branched amino acid mixture | collagen-composing amino acid mixture | 2 kinds of amino acid mixture | arginine | glutamine |
| Isoleucine | 16.7 | 21.8 | 22.2 | 12.0 | 32.5 | 1.7 | — | — | — |
| Leucine | 20.8 | 27.3 | 27.8 | 15.0 | 40.5 | 3.8 | — | — | — |
| Valine | 13.9 | 18.2 | 18.5 | 10.0 | 27.0 | 1.8 | — | — | — |
| Glutamine | 25.0 | 32.7 | — | 18 | — | — | 51.4 | — | 100 |
| Histidine | — | — | — | 5 | — | 0.9 | — | — | — |
| Lysine | — | — | — | 5 | — | 9.1 | — | — | — |
| Phenylalanine | — | — | — | 0.5 | — | 2.3 | — | — | — |
| Proline | — | — | — | 5 | — | 10.8 | — | — | — |
| Hydroxyproline | — | — | — | — | — | 8.8 | — | — | — |
| Threonine | — | — | — | 7 | — | 2.4 | — | — | — |
| Methionine | — | — | — | 5 | — | 0.7 | — | — | — |
| Alanine | — | — | — | — | — | 7.4 | — | — | — |
| Aspartic acid | — | — | — | — | — | 5.7 | — | — | — |
| Glutamic acid | — | — | — | — | — | 9.1 | — | — | — |
| Glycine | — | — | — | — | — | 24.2 | — | — | — |
| Tryptophan | — | — | — | 1 | — | — | — | — | — |
| Serine | — | — | — | — | — | 4.4 | — | — | — |
| Arginine | 23.6 | — | 31.5 | 17.0 | — | 6.8 | 48.6 | 100 | — |
| Total (%) | 100.0 | 100.0 | 100.0 | 100.0 | 100.0 | 100.0 | 100.0 | 100.0 | 100.0 |
| Amount administered | 0.432 g/kg/h | 0.330 g/kg/h | 0.324 g/kg/h | 0.6 g/kg/h | 0.220 g/kg/h | 0.6 g/kg/h | 0.220 g/kg/h | 0.5 g/kg/h | 0.42 g/kg/h |

The administration fluids were each administered continuously into the jugular vein for approximately three and a half hours. Stable isotope-labelled L-phenylalanine was used to determine the rate of collagen synthesis by measuring the labelled percentage of stable isotope-labelled L-phenylalanine that had been incorporated in collagen protein within a fixed period of time. Skin was used as the tissue, and fractions of newly synthesized collagen dissoluble in a neutral salt solution were used as the collagen. The results are shown in FIG. 1 below.

The group administered with physiological saline was used as the control, and assay was conducted by t-test. The symbol * in the FIGURE represents $p<0.05$. The method of calculation is shown by the following formula (1).

$$\text{Rate of collagen synthesis} = \Delta Et/\Delta Ef/\Delta T \quad (1)$$

ΔEt: labelled percentage of the phenylalanine in collagen fractions per unit time 5 or 4 kinds of amino acids in comparison with for the group administered with the mixture of 12 kinds of amino acids (denoted by "AVP" in the FIGURE) or the collagen-composing amino acid composition, it was indicated that the compositions of 5 kinds or 4 kinds of amino acids possess an extremely excellent effect for promotion of collagen synthesis.

The invention claimed is:

1. A method for promoting collagen synthesis, comprising administering to a subject in need thereof an effective amount of a composition comprising:
    (a) 10 to 40 parts by weight of L-arginine or L-glutamine;
    (b) 5 to 20 parts by weight of L-valine;
    (c) 8 to 30 parts by weight of L-isoleucine; and
    (d) 10 to 35 parts by weight of L-leucine.

2. The method of claim 1, wherein said composition comprises 10 to 40 parts by weight of L-arginine.

3. The method of claim 1, wherein said composition comprises 10 to 40 parts by weight of L-glutamine.

4. The method of claim 1, wherein said composition comprises 10 to 40 parts by weight of L-arginine and 10 to 40 parts by weight of L-glutamine.

5. A method for inhibiting an effect of skin aging, comprising administering to a subject in need thereof an effective amount of a composition comprising:
  (a) 10 to 40 parts by weight of L-arginine or L-glutamine;
  (b) 5 to 20 parts by weight of L-valine;
  (c) 8 to 30 parts by weight of L-isoleucine; and
  (d) 10 to 35 parts by weight of L-leucine.

6. The method of claim 5, wherein said composition comprises 10 to 40 parts by weight of L-arginine.

7. The method of claim 5, wherein said composition comprises 10 to 40 parts by weight of L-glutamine.

8. The method of claim 5, wherein said composition comprises 10 to 40 parts by weight of L-arginine and 10 to 40 parts by weight of L-glutamine.

9. A method for suppressing osteoporosis, comprising administering to a subject in need thereof an effective amount of a composition comprising:
  (a) 10 to 40 parts by weight of L-arginine or L-glutamine;
  (b) 5 to 20 parts by weight of L-valine;
  (c) 8 to 30 parts by weight of L-isoleucine; and
  (d) 10 to 35 parts by weight of L-leucine.

10. The method of claim 9, wherein said composition comprises 10 to 40 parts by weight of L-arginine.

11. The method of claim 9, wherein said composition comprises 10 to 40 parts by weight of L-glutamine.

12. The method of claim 9, wherein said composition comprises 10 to 40 parts by weight of L-arginine and 10 to 40 parts by weight of L-glutamine.

13. A method for promoting regeneration of tendon and ligament, comprising administering to a subject in need thereof an effective amount of a composition comprising:
  (a) 10 to 40 parts by weight of L-arginine or L-glutamine;
  (b) 5 to 20 parts by weight of L-valine;
  (c) 8 to 30 parts by weight of L-isoleucine; and
  (d) 10 to 35 parts by weight of L-leucine.

14. The method of claim 13, wherein said composition comprises 10 to 40 parts by weight of L-arginine.

15. The method of claim 13, wherein said composition comprises 10 to 40 parts by weight of L-glutamine.

16. The method of claim 13, wherein said composition comprises 10 to 40 parts by weight of L-arginine and 10 to 40 parts by weight of L-glutamine.

* * * * *

UNITED STATES PATENT AND TRADEMARK OFFICE
CERTIFICATE OF CORRECTION

PATENT NO. : 7,645,796 B2 Page 1 of 1
APPLICATION NO. : 11/477436
DATED : January 12, 2010
INVENTOR(S) : Hitoshi Murakami et al.

It is certified that error appears in the above-identified patent and that said Letters Patent is hereby corrected as shown below:

Title page, Item (75) Inventors: Should read as follows: --Hitoshi Murakami, Kawasaki-shi (JP);
Hisamine Kobayashi, Kawasaki-shi (JP)--;

Abstract, line 5, "ofL", Should read --of L--;
Column 2, Line 24, "ofL", Should read --of L--.

Signed and Sealed this

Tenth Day of August, 2010

David J. Kappos
*Director of the United States Patent and Trademark Office*